(12) United States Patent
Jin et al.

(10) Patent No.: US 11,224,440 B2
(45) Date of Patent: Jan. 18, 2022

(54) RELEASE DEVICE FOR MEDICAL TISSUE CLIPS

(71) Applicant: Micro-Tech (Nanjing) Co., Ltd., Jiangsu (CN)

(72) Inventors: Hongyan Jin, Nanjing (CN); Derong Leng, Nanjing (CN); Changqing Li, Nanjing (CN); Weiqin Qiu, Nanjing (CN); Ran Song, Nanjing (CN)

(73) Assignee: MICRO-TECH (NANJING) CO., LTD., Nanjing (CN)

( * ) Notice: Subject to any disclaimer, the term of this patent is extended or adjusted under 35 U.S.C. 154(b) by 202 days.

(21) Appl. No.: 16/605,817

(22) PCT Filed: Mar. 26, 2018

(86) PCT No.: PCT/CN2018/080448
§ 371 (c)(1),
(2) Date: Oct. 17, 2019

(87) PCT Pub. No.: WO2018/228020
PCT Pub. Date: Dec. 20, 2018

(65) Prior Publication Data
US 2020/0146685 A1    May 14, 2020

(30) Foreign Application Priority Data
Jun. 12, 2017  (CN) .......................... 201710439621.3

(51) Int. Cl.
*A61B 17/128* (2006.01)
*A61B 17/08* (2006.01)
(Continued)

(52) U.S. Cl.
CPC ........ *A61B 17/1285* (2013.01); *A61B 17/083* (2013.01); *A61B 17/122* (2013.01);
(Continued)

(58) Field of Classification Search
CPC ............. A61B 17/083; A61B 17/1285; A61B 17/122; A61B 17/08; A61B 17/10; A61B 2017/00862; A61B 2017/12004
See application file for complete search history.

(56) References Cited

U.S. PATENT DOCUMENTS 9,795,390 B2   10/2017   Jin
10,470,775 B2  11/2019   Shi
(Continued)

FOREIGN PATENT DOCUMENTS

CN   102626335 A   8/2012
CN   102727276 A   10/2012
(Continued)

OTHER PUBLICATIONS

Communication pursuant to Article 94(3) EPC for European Patent Application No. 18 817 602.8, dated Feb. 14, 2020, 7 pages.
(Continued)

*Primary Examiner* — Katherine M Rodjom
(74) *Attorney, Agent, or Firm* — Mai-Tram D. Lauer; Westman, Champlin & Koehler, P.A.

(57) ABSTRACT

Provided is a release device for medical tissue clips, including an outer tube provided with a release member, a control wire, and at least one tissue clip; wherein the release member is connected to the distal end of the control wire; the at least one tissue clip is movably connected to the release member and the control wire; the tissue clip includes a clip base and a clip piece which is movably disposed inside the clip base; the tissue clip is in a locked state when the clip piece is retreated to the proximal end, and in an opened state when the clip piece moves forwards to the distal end; the clip base includes an elastic member which is in a compressed
(Continued)

state when being located in the outer tube and in an opened state upon detachment from the outer tube to abut against an end of the outer tube.

13 Claims, 7 Drawing Sheets

(51) Int. Cl.
 *A61B 17/122* (2006.01)
 *A61B 17/00* (2006.01)
 *A61B 17/12* (2006.01)
(52) U.S. Cl.
 CPC .............. *A61B 2017/00862* (2013.01); *A61B 2017/12004* (2013.01)

(56) References Cited

U.S. PATENT DOCUMENTS

| | | | | |
|---|---|---|---|---|
| 2008/0281353 | A1* | 11/2008 | Aranyi | A61B 17/064 606/219 |
| 2015/0073439 | A1* | 3/2015 | Dannaher | A61B 17/10 606/142 |
| 2017/0281176 | A1 | 10/2017 | Maekubo et al. | |
| 2018/0344323 | A1 | 12/2018 | Shi | |

FOREIGN PATENT DOCUMENTS

| | | |
|---|---|---|
| CN | 202699217 U | 1/2013 |
| CN | 205831589 U | 12/2016 |
| CN | 107280723 A | 10/2017 |
| CN | 207707958 U | 8/2018 |
| JP | 2008-119526 A | 5/2008 |
| JP | 3159938 U | 6/2010 |
| JP | 2012196376 A | 10/2012 |
| WO | 2016/104075 A1 | 6/2016 |
| WO | 2017/066987 A1 | 4/2017 |
| WO | WO-2017066986 A1 * | 4/2017 ........... A61B 17/128 |

OTHER PUBLICATIONS

Supplemental search document for Chinese Patent Application No. 201710439621.3 (foreign priority), filed Jun. 12, 2017, 1 page.
Notification of Reasons for Refusal for Japanese Patent Application No. 2019-555030, date of drafting Mar. 2, 2021, 10 pages.
International Search Report and Written Opinion for International Application No. PCT/CN2018/080448, dated Jul. 6, 2018, 16 pages.

* cited by examiner

RELEASE DEVICE FOR MEDICAL TISSUE CLIPS

PRIORITY

This application is a U.S. national application of the international application number PCT/CN2018/080448 filed on May 26, 2018, which claims priority of Chinese application CN201710439621.3 filed on Jun. 12, 2017 the contents of all of which are incorporated herein by reference.

TECHNICAL FIELD

The present disclosure relates to the field of medical apparatuses, and in particular to a release device for medical tissue clips.

BACKGROUND ART

Medical tissue clips clamp tissues using the mechanical squeezing principle so that wounds are closed, and they can also be used to compress blood vessels to achieve the effect of rapid hemostasis. Such tissue clips made of metal have been adopted and used by medical institutions all over the world for recent decades due to its advantages such as fast speed, reliable clamping, small trauma, and less complications in terms of wound closure and hemostasis, and have become a means which is extremely effective for postoperative suture of a critical patient suffered with an acute gastrointestinal surgery and surgical treatment of hemorrhage in critical patients, and is of a great value in clinical application. This metal tissue clip can be skillfully operated by a doctor to effectively perform wound closure or hemostasis, and prevent rebleeding, and also greatly improve the safety and cure rate of gastrointestinal endoscopic treatments, however the tissue clips commonly used in the prior clinical surgeries are mostly single-firing clips. If the wound is large in size or has multiple bleeding spots, the tissue clip needs to be released multiple times and needs to be relocated, whereby a very large workload is involved in the surgery performed by the doctor, and it takes a lot of time to repeatedly insert and withdraw the delivery device for tissue clips. As a result, the course of surgery lasts too long, and even the worse, the most appropriate timing of hemostasis is missed, which results in troubles caused by excessive bleeding in the patient's gastrointestinal tract.

SUMMARY

Object of the Disclosure: the technical problem to be solved by the present disclosure is to provide a release device for medical tissue clips in view of the deficiencies of the prior art.

In order to solve the above technical problems, the present disclosure provides a release device for medical tissue clips, comprising an outer tube provided with one release member, a control wire, and at least one tissue clip, wherein the one release member is connected to the distal end of the control wire, and the at least one tissue clip is movably connected to the release member and the control wire;

the tissue clip comprises a clip base and a clip piece, the clip piece is movably disposed inside the clip base, the tissue clip is configured to be in a locked state when the clip piece is retreated to a proximal end of the clip base, and in an opened state when the clip piece is moved frontward to a distal end of the clip base; the clip base comprises an elastic member, the elastic member is configured to be in a pressed state when it is located in the outer tube, and in an opened state upon detachment from the outer tube so as to abut against an end portion of the outer tube to prevent the tissue clip from retreating into the outer tube; a distal end through hole, a middle envelope through hole, and a proximal end through hole through which allow the release member to pass through are provided at the distal end, middle segment, and proximal end of the clip piece, and all the tissue clips are sequentially connected in series to the release member and the control wire through the distal end through hole, the middle envelope through hole, and the proximal end through hole;

the release member comprises a push portion and a pull portion; the push portion is configured to push the clip base and the clip piece out of the outer tube; and the pull portion is configured to pull the clip piece so as to be completely retreated to the proximal end after the elastic member of the clip base abuts against the end portion of the outer tube; and after the release member pulls the clip piece so as to be completely retreated to the proximal end, the release member is separated from the clip piece, whereby the release of the tissue clip is achieved.

In the present disclosure, the tissue clip includes two or more tissue clips sequentially connected in series to the control wire.

In the present disclosure, the outer tube may be bourdon tube.

In the present disclosure, a portion around the proximal end through hole of the clip piece is made of an elastic material, and after a certain pulling force is applied to the release member, the push portion drives the proximal end through hole of the clip piece to be deformed and become larger, and the push portion slides through the proximal end through hole of the clip piece toward the proximal end, so that the proximal end through hole of the clip piece is located between the push portion and the pull portion of the release member such that the release member can push the clip piece and the clip base out of the outer tube.

In the present disclosure, when a pulling force applied to the release member is greater than a preset value, the pull portion drives the proximal end through hole of the clip piece to be deformed and then become larger, and the pull portion is detached from the proximal end through hole of the clip piece, whereby separation of the release member from the clip piece is achieved.

In the present disclosure, the push portion of the release member may be made of an elastic material, and when a certain pulling force is applied to the release member, the push portion is compressively deformed and then becomes smaller, and the push portion slides through the proximal end through hole of the clip piece, so that the proximal end through hole of the clip piece is located in the groove portion of the release member, such that the release member can push the clip piece and the clip base out of the outer tube.

In the present disclosure, the pull portion of the release member may be made of an elastic material, and when a pulling force applied to the release member is greater than a preset value, the pull portion is compressively deformed and then becomes smaller, and the pull portion is detached from the proximal end through hole of the clip piece, whereby separation of the release member from the clip piece is achieved.

In the present disclosure, the pull portion of the release member is a first protrusion portion, the push portion is a second protrusion portion, a groove portion is provided at the proximal end of the first protrusion portion, a diameter of the groove portion is smaller than diameters of the first protrusion portion and the second protrusion portion, a diameter of a joint between the groove portion and the first protrusion portion gradually increases from the proximal end to the distal end, a diameter of a proximal end portion of the second protrusion portion gradually decreases from the distal end to the proximal end, and a first abutment surface is provided at a joint between the groove portion and the second protrusion portion.

In the present disclosure, the elastic member of the clip base is a first blade, the clip base is further provided with a clip base slot, the clip piece comprises two clip piece bodies, the two clip piece bodies have a proximal end through hole which is a first hole matched with the release member, and have a distal end through hole which is a second hole, a second blade matched with the clip base slot is provided on both sides of the first hole, and a clip piece end surface matched with the first abutment surface is provided at the proximal end of the clip piece.

In the present disclosure, the distal ends of the two clip piece bodies each have a half through hole when the clip piece is configured to be in an opened state, and when the clip piece is configured to be in the locked state, where the two clip piece bodies are closed, the half through holes at the distal ends of the two clip pieces form the second hole.

In the present disclosure, a diameter of the first protrusion portion is larger than a diameter of the second protrusion portion, and the diameter of the second protrusion portion is larger than an inner diameter of the first hole of the clip piece.

In the present disclosure, when the clip piece is configured to be in the locked state, the two clip piece bodies are closed, and an inner diameter of the second hole formed at the distal end is larger than the diameter of the first protrusion portion of the release member. In this way, all the tissue clips can be serially connected to the release member In the present disclosure, the diameter of the second protrusion portion is slightly smaller than the diameter of the first protrusion portion.

In the present disclosure, the distal end of the outer tube is provided with a support cap, and the support cap is provided with a second abutment surface.

In the present disclosure, the proximal end of the release member is connected to the control wire, an inner plastic tube is disposed on an outer circumference of the control wire, the proximal end of the control wire is connected to a drive tube, the drive tube is connected to a rack, the rack is engaged with a gear, a boosting tube is disposed at the distal end of the handle, a proximal end of the boosting tube is connected to the drive tube and the control wire, and the distal end of the boosting tube is sleeved on the inner plastic tube.

In the present disclosure, the release member is connected to a handle via the control wire, a handwheel is disposed outside the handle, and a gear, a rack, a drive tube, and a boosting tube are disposed in the handle; the handwheel is rotated to sequentially drive the gear, the rack, the drive tube, the boosting tube and the control wire, and the control wire drives the release member.

Advantageous Effects

A release device for medical tissue clip according to the present disclosure greatly reduces the course of surgeries, and maximally solves the drawback that it is typically required multiple replacements of release devices for tissue clip due to unstoppable bleeding or excessive wound in clinical practice.

BRIEF DESCRIPTION OF DRAWINGS

The present disclosure will be described further specifically with reference to the accompanying drawings and particular embodiments, and the advantages of the present disclosure in the above or other aspects will become more apparent.

Figure 1:
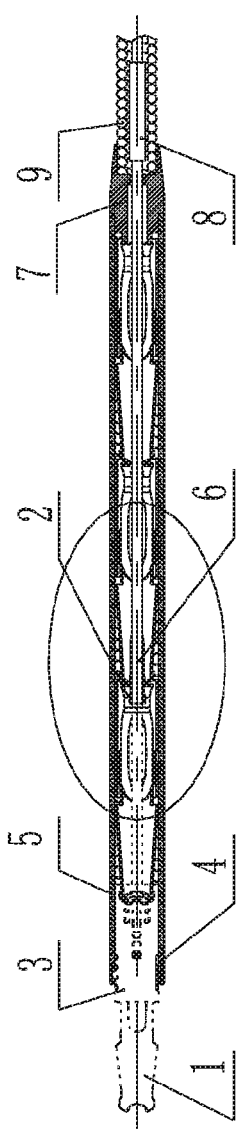
FIG. 1 is a sectional view of a distal end release portion according to the present disclosure.

REFERENCE NUMERALS 1, clip piece; 2, release member; 3, clip base; 4, support cap; 5, outer tube; 6, control wire; 7, connector; 8, lining tube; 9, second outer tube; 10, inner plastic tube; 11, boosting tube; 12, sheath outer tube; 13, sleeve; 14, drive tube; 15, rack; 16, gear; 17, handwheel; 18, handle cover (right); 19, handle cover (left); 101, first hole; 102, second hole; 103, clip piece end surface; 104, second hole; 105, clip arm tail portion; 106, middle envelope through hole; 201, first protrusion portion; 202, groove portion; 203, second protrusion portion; 204, first abutment surface; 205, distal end projection portion of the release member; 206, proximal end projection portion of the release member; 207, first elastic deformation portion of the release member; 208, second elastic deformation portion of the release member; 301, elongated slot of the clip base; 302, hanging platform; 303, first blade; 401, second abutment surface.

DETAILED DESCRIPTION OF EMBODIMENTS

The present disclosure will be described in detail below with reference to the accompanying drawings.

First Embodiment

As shown in FIG. 1, a front (or proximal) end release portion of a release device for medical tissue clip comprises a clip piece 1, a release member 2, a clip base 3, a support cap 4, an outer tube 5, a control wire 6, a connector 7, a lining tube 8, and a second outer tube 9, wherein the clip piece 1 and the clip base 3 constitute a tissue clip, a set of tissue clips are movably connected to the release member 2, the support cap 4 is disposed at the distal end of the outer tube 5, the proximal end of the release member 2 is connected to the control wire 6, the connector 7, the lining tube 8, and the second outer tube 9 are disposed at the proximal end of the outer tube 5, the connector 7 is configured to connect the outer tube 5 and the second outer tube 9, and the lining tube 8 is disposed on an outer circumference of the control wire 6 and configured to control a movement stroke of the tissue clip.

Figure 2:
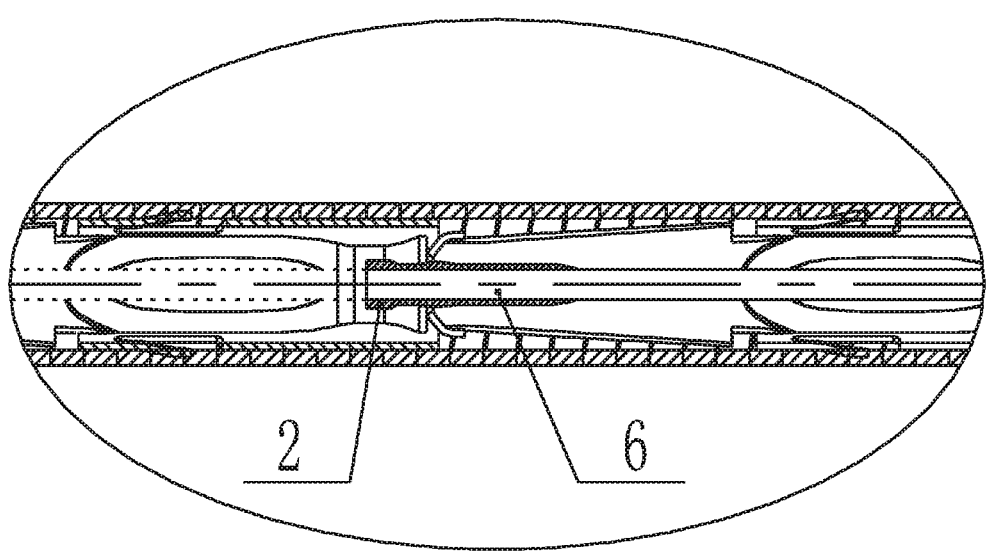
FIG. 2 is a partial enlarged view of FIG. 1.

As shown in FIG. 2, the proximal end of the release member 2 is connected to the control wire 6, which is made of a steel wire in the present embodiment.

Figure 3:
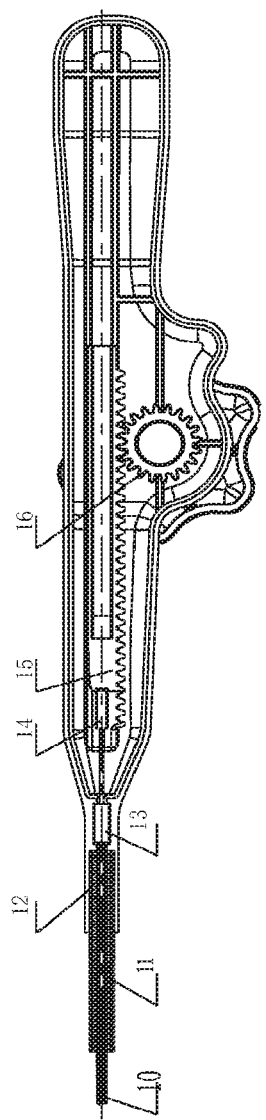
FIG. 3 is a schematic view of a proximal end handle portion according to the present disclosure.
Figure 4:
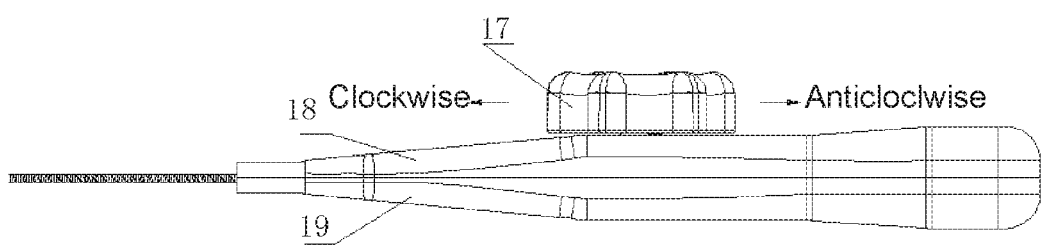
FIG. 4 is a schematic view of the proximal end handle portion according to the present disclosure.

As shown in FIG. 3 and FIG. 4, a proximal end handle portion is composed of an inner plastic tube 10, a boosting tube 11, a sheath outer tube 12, a sleeve 13, a drive tube 14, a rack 15, a gear 16, a handwheel 17, a handle cover (right) 18, and a handle cover (left) 19. The proximal end of the release member 2 is connected to a handle, the handwheel 17 is disposed outside the handle, the gear 16, the rack 15, and the drive tube 14 are disposed in the handle, the inner plastic tube 10 is disposed on the outer circumference of the control wire 6, the proximal end of the control wire 6 is connected to the drive tube 14, the drive tube 14 is connected to the rack 15, the rack 15 is engaged with the gear 16, and the handwheel 17 is rotated to sequentially drive the gear 16, the rack 15, and the drive tube 14, and the drive tube 14 drives the release member 2.

Figure 5:
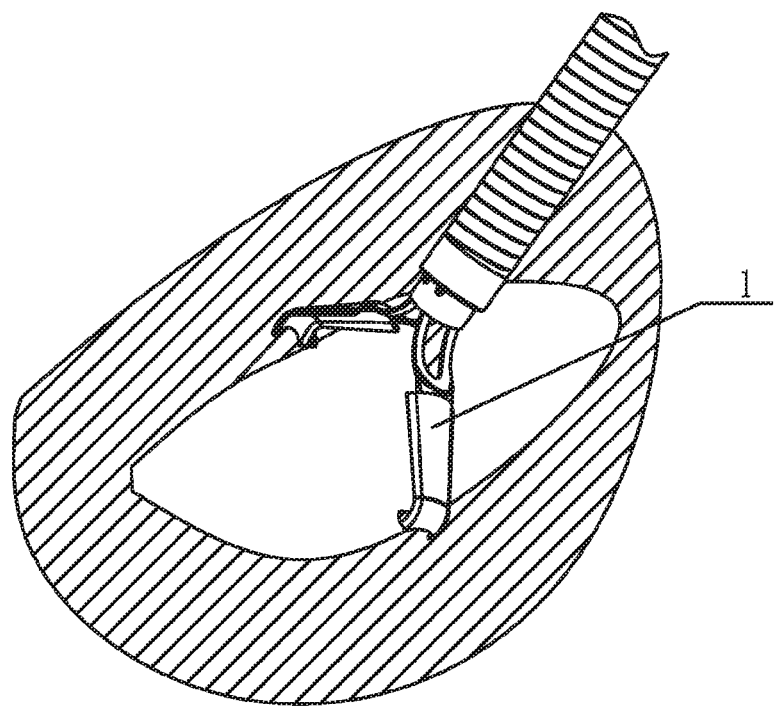
FIG. 5 is a schematic view showing a tissue clip positioned at a wound according to the present disclosure.

FIG. 5 shows a schematic view of use of the tissue clip.

Figure 6:
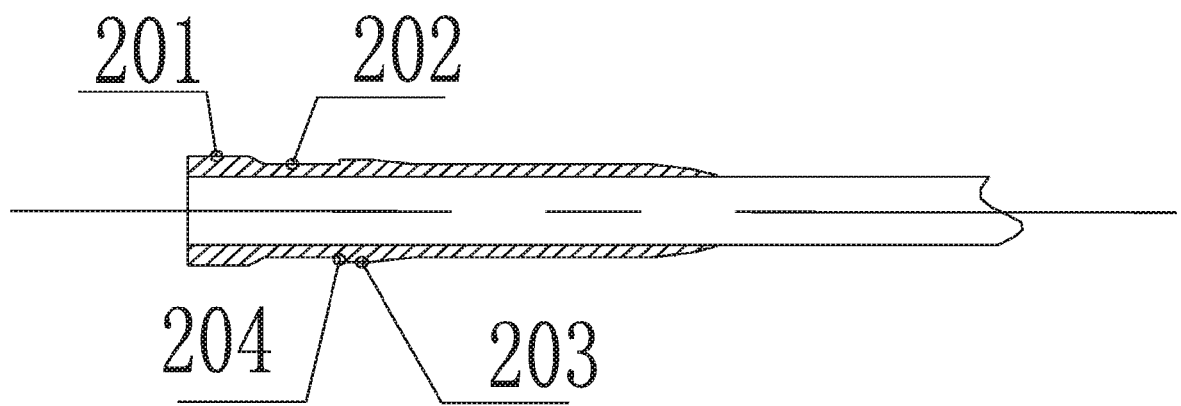
FIG. 6 is an enlarged schematic view of a release member according to the present disclosure.

As shown in FIG. 6, the release member 2 comprises a first protrusion portion 201, a groove portion 202, a second protrusion portion 203, and a first abutment surface 204, wherein the first protrusion portion 201 is provided at the distal end of the release member 2, the groove portion 202 is provided at the proximal end of the first protrusion portion, the second protrusion portion 203 is provided at the proximal end of the groove portion, the diameter of the groove portion 202 is smaller than the diameters of the first protrusion portion 201 and the second protrusion portion 203, the diameter of a joint between the groove portion 202 and the first protrusion portion 201 gradually increases from the proximal end to the distal end, and the first abutment surface 204 is disposed at a joint between the groove portion 202 and the second protrusion portion 203.

Figure 7:
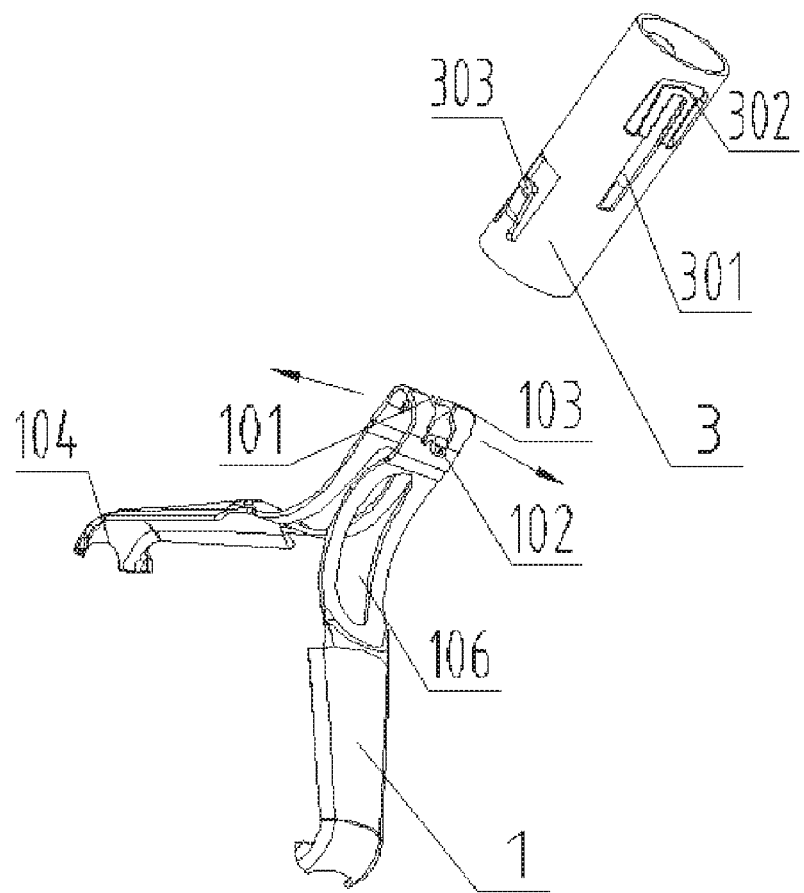
FIG. 7 is an exploded view of the tissue clip according to the present disclosure.

As shown in FIG. 7, the tissue clip comprises a clip base 3 and a clip piece 1, the clip base is provided with a first blade 303 and a hanging platform 302, the clip piece comprises two clip piece bodies, a first hole 101 is provided in a joint between the two clip piece (1) bodies, a second blade 102 matched with the hanging platform 302 is disposed at each of both ends of the first hole 101, and a clip piece end surface 103 matched with the first abutment surface 204 is provided at the proximal end of the clip piece 1. The provision of a middle envelop through hole 106 in the clip piece is configured to facilitate the serial connection of all the tissue clips to the control wire 6, and also facilitate the passage of the release member 2 therethrough. When the tissue clip is configured to be in a pressed state, the two clip piece bodies are closed together, and thus the tissue clips cannot be serially connected to the control wire 6 and the release member 2 cannot pass therethrough if the middle envelope through hole 106 is not provided.

Figure 8:
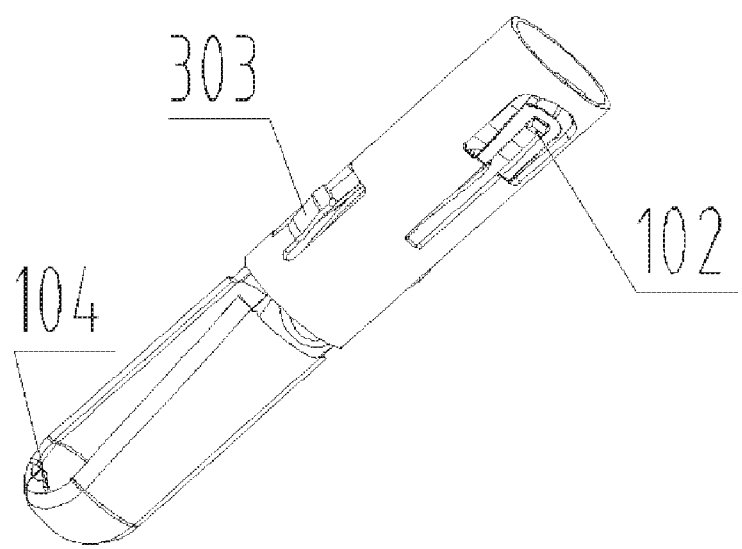
FIG. 8 is a schematic view showing a tissue clip in a closed state according to the present disclosure.

FIG. 8 shows a schematic view showing a tissue clip in a closed state. When the clip piece is configured to be in the opened state, each of the distal ends of the two clip piece bodies has a half through hole. When the clip piece is configured to be in the locked state, the two clip piece bodies are closed, and the half through holes at the distal end form a second hole 104.

Figure 9:
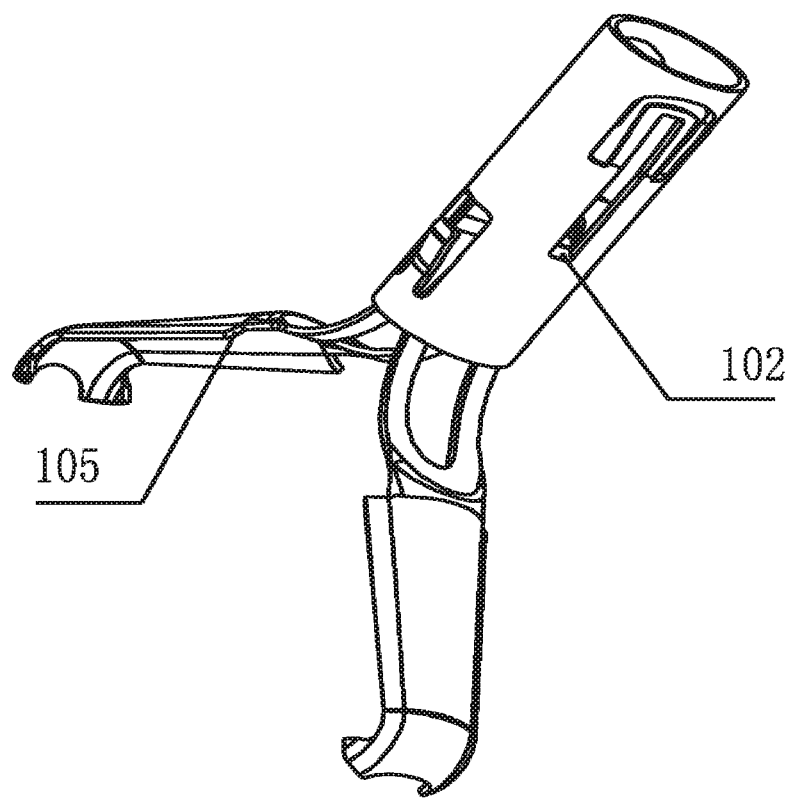
FIG. 9 is a schematic view showing a tissue clip in an opened state according to the present disclosure.

FIG. 9 shows a schematic view showing the tissue clip in an opened state.

Figure 10:
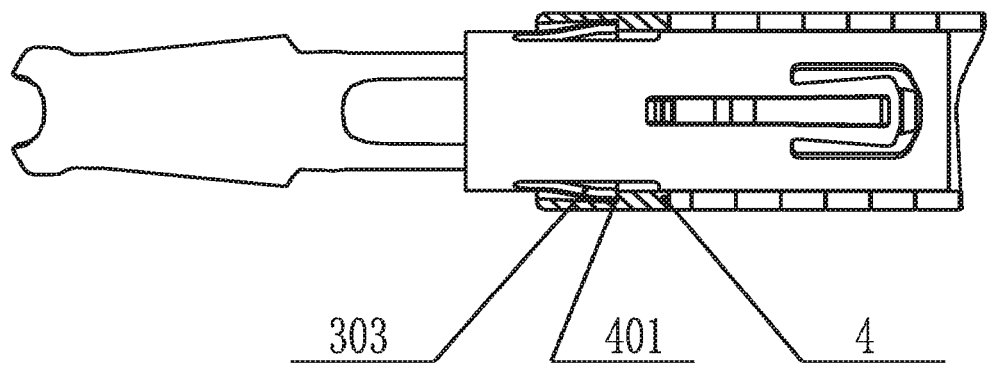
FIG. 10 is a schematic view showing a position of the tissue clip before being released according to the present disclosure.

FIG. 10 shows a schematic view showing a position of the tissue clip before being released, wherein the first blade 303 abuts against the second abutment surface 401.

Principle of Use:

Release of a First Tissue Clip: FIG. 1 shows the distal end release portion which has been assembled, wherein three tissue clips are connected in series inside the outer tube 5 located at the distal end, the three tissue clips are all configured to be in the closed state, and a tissue clip represented by a dotted line at the distal end in FIG. 1 is shown to simulate a state of the first tissue clip after being pushed out from the outer tube; the handwheel 17 of FIG. 3 and FIG. 4 is rotated clockwise to push out the first tissue clip to the position of the tissue clip represented by the dotted line shown in FIG. 1, and the tissue clip is automatically opened under the action of an elastic force. At this time, the first blade 303 of the clip base abuts against the second abutment surface 401 of the support cap at the distal end of the outer tube and is kept stationary, and the corresponding angle is finely adjusted so that effective clamping of the tissue by the clip piece 1 is ensured in the state as shown in FIG. 5, and then the handwheel 17 is rotated counterclockwise to pull the tissue clip back toward the proximal end so that the two clip piece bodies are closed to clamp a site to be hemostatic; then the reverse rotation of the handwheel 17 is continued with an increased rotational force to continue pulling the tissue clip back toward the proximal end, the first protrusion 201 and a tapered angle at its proximal end cause the first hole 101 at the tail end of the clip piece to be elastically and plastically deformed (a direction shown by the arrows in FIG. 7 is a direction in which it is elastically deformed), so that the release member 2 is disengaged from the first hole 101 of the tissue clip toward the proximal end, the handwheel 17 is then rotated clockwise, and the first tissue clip is completely pushed out of the outer tube 5 using the distal end of the release member 2, whereby the release of the first tissue clip is completed.

Release of a Second Tissue Clip: When the wound is too large in size, multiple tissue clips are required to close the wound. The handwheel 17 is rotated counterclockwise to pull the groove portion 202 of the release member 2 in FIG. 6 back to the position of the first hole 101 of the (second) clip piece 1 in FIG. 7. During this process, the first hole 101 of the clip piece 1 will be slightly opened (elastically deformed) under the action of the second protrusion portion 203 which is a central tapered step of the release member 2, so that the second protrusion portion 203 of the release member 2 can pass through the first hole 101 of the clip piece 1. When the first hole 101 of the clip piece 1 is at the position of the groove portion 202 of the release member 2, the first hole 101 of the clip piece 1 will be restored to the original size. At this time, due to the presence of the first abutment surface 204 which is a distal end surface of the second protrusion portion 203 of the release member 2, the operator can repeat the action of releasing the first tissue clip to complete the release of the second tissue clip.

The above actions are repeated until all the tissue clips are completely released.

As shown in FIG. 7, FIG. 8 and FIG. 9, the clip piece 1 of the tissue clip is configured to be in the closed state when it is located inside the outer tube 5 located at the distal end, and the clip piece 1 is configured to be in the opened state when it is pushed out of the outer tube 5 located at the distal end, and the stroke of the change depends on the position of the second blade 102 at an elongated slot 301 of the clip base.

As shown in FIG. 6, FIG. 7, and FIG. 8, when the tissue clip is to be released, a force required for pulling the first protrusion portion 201 of the release member 2 out of the first hole 101 must be greater than a force for pulling the second blade 102 into the position of the hanging platform 302; when the second blade 102 is pulled into the position of the hanging platform 302, the clip arm tail portion 105 of the clip piece 1 will be caught at the distal end surface of the clip base 3; as shown in FIG. 10, before the tissue clip is released, the first blade 303 of the clip base 3 abuts against the inner stepped end surface of the support cap 4, whereby effective detachment of the release member from the tissue clip is ensured. The bevel angle arranged at the proximal end of the first protrusion portion 201 of the release member 2 can provide good adjustment and guidance of the release force for pulling and detachment of the tissue clip from the release member.

In this example, the release member 2 is made of a stainless steel material, and its cross section is not limited to a circular shape, and may include various shapes such as an elliptical shape and a polygonal shape; and the cross-sectional shape of the release member is matched with the shape of the first hole 101 to facilitate the release.

The second blade 102 of the clip piece 1 interacts with the elongated slot 301 of the clip base, which not only restricts the rotation of the clip piece 1 in the clip base 3, but also controls an axial stroke of the clip piece 1.

During the release of the tissue clip, the first blade 303 of the clip base 3 abuts against the inner stepped end surface of the support cap 4 and interacts with the release force to ensure the effective detachment and closure of the tissue clip.

In FIG. 1, since the next two tissue clips are in a relatively static state in the tube after the first tissue clip is released, it is necessary to pull the release member 2 backward to the position where the second tissue clip is located in FIG. 1 when the second tissue clip needs to be released; the first abutment surface 204 of the release member 2 in FIG. 6 is abutted against the clip piece end surface 103 of the clip piece 1 in FIG. 7, and at this time the second blade 102 is located at the position shown in FIG. 9, and the outer diameter of the second protrusion portion 203 should be larger than the inner diameter of the first hole 101 so that it is ensured that the first abutment surface 204 can effectively abut against the end surface 103 of the clip piece; and the third or further more tissue clips are released stepwise in the manner in which the first tissue clip is released.

The outer diameter of the second protrusion portion 203 should be larger than the inner diameter of the first hole 101, so that the release member 2 can successfully push the tissue clip out of the outer tube 5 located at the distal end.

The outer diameter of the first protrusion portion 201 of the release member 2 should be larger than the outer diameter of the second protrusion portion 203 so that the tissue clip can be effectively detached and locked, and the proximal end of the first protrusion portion 201 is required to be provided with an effective chamfer to enhance the guiding property so that the release member 2 can be successfully pulled out.

In order to keep the tissue clip within a controllable range, it is necessary to use the lining tube 8 to control the stroke of pushing of each tissue clip out of the outer tube 5 located at the distal end. In the tissue clip represented by the dotted line as shown in FIG. 1, it should be ensured that the first blade 303 of the clip base 3 is within the range of the second abutment surface 401 of the support cap 4.

The proximal end handle portion may be driven by cooperation of a gear and a rack, or may be driven by means of direct pushing or the like, for releasing the tissue clip. Here, a scale may be provided in the handwheel to control the accuracy of the release of each tissue clip.

Second Embodiment

Figure 11:
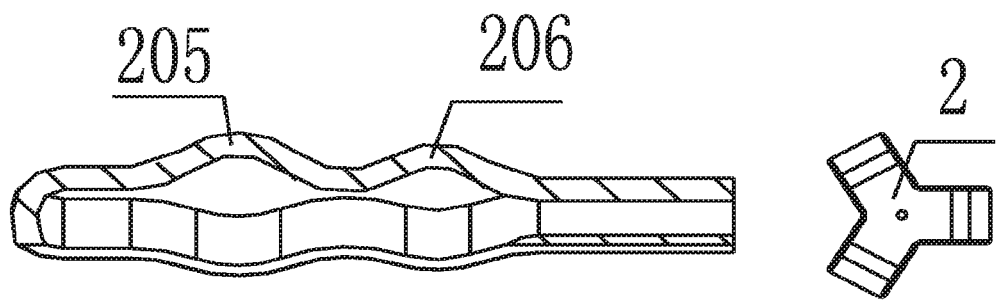
FIG. 11 is a fully sectional schematic view of a release member of a second embodiment.
Figure 12:
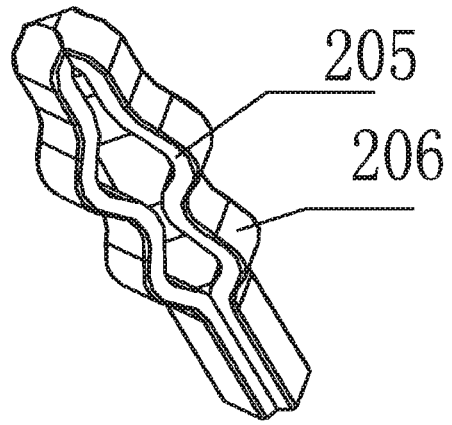
FIG. 12 is a schematic perspective view of the release member of the second embodiment.

As shown in FIG. 11 and FIG. 12, in the present embodiment, the release member 2 comprises two arcuate projection portions, which are a distal end projection portion 205 of the release member and a proximal end projection portion 206 of the release member. The release member 2 is made of an elastic material (such as a nickel-titanium alloy material), and in this embodiment, the corresponding tissue clip is received, pushed, and released by using the elastic deformations of the distal end projection portion 205 of the release member and the proximal end projection portion 206 of the release member.

Third Embodiment

Figure 13:
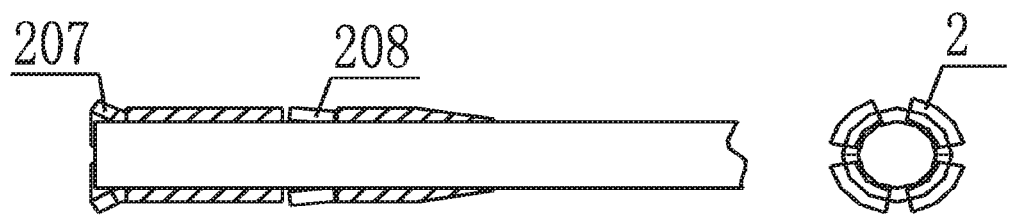
FIG. 13 is a schematic view of a release member of a third embodiment.
Figure 14:
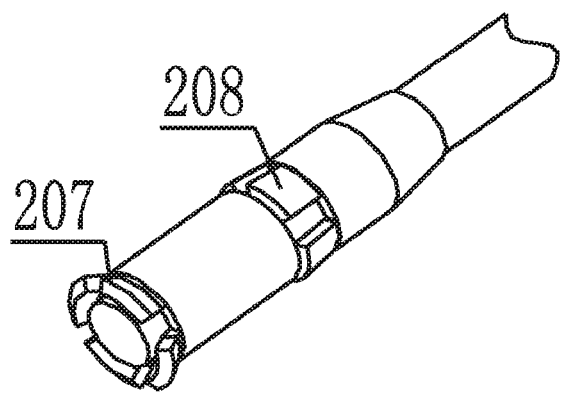
FIG. 14 is a schematic perspective view of the release member of the third embodiment.

As shown in FIG. 13 and FIG. 14, in the present embodiment, the release member 2 comprises a first elastic deformation portion 207 of the release member and a second elastic deformation portion 208 of the release member, and the corresponding tissue clip is received, pushed, and released by using the elastic deformations of the first elastic deformation portion 207 of the release member and the second elastic deformation portion 208 of the release member.

Fourth Embodiment

The present embodiment is different from the first embodiment in that there is only one tissue clip, and the release member 2 is directly mounted in the proximal end through hole (i.e., the first hole 101) of the clip piece 1, so that the proximal end through hole (i.e., the first hole 101) is located in the groove portion 202 of the release member 2 and disposed in the outer tube, and the clip piece 1 in this case may not be provided with the second hole 104 and the middle envelop through hole 106.

The present disclosure provides a release device for medical tissue clip, and the technical solution can be specifically implemented by many methods and in many ways. The above description is merely illustrative of preferred embodiments of the present disclosure. It should be noted that, as understood by those skilled in the art, a number of improvements and modifications may be made without departing from the principles of the present disclosure, and such improvements and modifications should also be considered to be within the scope of protection of the present disclosure. All the components that are not clearly described in the embodiments of the present disclosure can be implemented by the prior art.

What is claimed is:

1. A release device for medical tissue clips, comprising an outer tube located at a distal end, one release member, a control wire, and a plurality of tissue clips, wherein the one release member, the control wire, and the tissue clips are disposed in the outer tube, the one release member is connected to a distal end of the control wire, and the tissue clips are movably connected to the release member and the control wire;
    each tissue clip of the plurality of tissue clips comprising a clip base and a clip piece, wherein the clip piece is movably disposed inside the clip base, each tissue clip is configured to be in a locked state when the clip piece is retreated to a proximal end of the clip base, and in an opened state when the clip piece is moved frontward to a distal end of the clip base;
    the clip base comprising an elastic member, wherein the elastic member is configured to be in a pressed state when located in the outer tube, and in an opened state upon detachment from the outer tube so as to abut against an end portion of the outer tube to prevent the tissue clip from retreating into the outer tube;
    a second hole, a middle envelope through hole and a first hole, each configured to allow the release member to pass through, and provided at the distal end, a middle segment, and a proximal end of the clip piece respectively, wherein the release member and the control wire are connected with each tissue clip through the second hole, the middle envelope through hole and the first hole; and
    the one release member comprising a single push portion and a single pull portion for the plurality of clips, wherein the push portion is configured to push the clip base and the clip piece of one of the plurality of clips out of the outer tube, and the pull portion is configured to pull the clip piece to be completely retreated to the proximal end of the clip base of the one of the plurality of clips after the elastic member of the clip base abuts against the end portion of the outer tube, wherein after the one release member pulls the clip piece to be completely retreated to the proximal end of the clip base, the one release member is separated from the clip piece, whereby a release of the one of the plurality of clips is completed.

2. The release device for medical tissue clips according to claim 1, wherein the plurality of tissue clips comprises two or more tissue clips sequentially connected in series to the control wire.

3. The release device for medical tissue clips according to claim 1, wherein a portion around a proximal end through hole of each clip piece is made of an elastic material, such that after a pulling force is applied to the one release member, the push portion drives the proximal end through hole of the clip piece to be deformed and become larger, and the push portion slides through the proximal end through hole of the clip piece toward the proximal end of the clip base, to make the proximal end through hole of the clip piece located between the push portion and the pull portion of the release member such that the release member can push the clip piece and the clip base out of the outer tube.

4. The release device for medical tissue clips according to claim 1, wherein after a pulling force applied to the one release member is greater than a preset value, the pull portion drives the proximal end through hole of the clip piece to be deformed and then become larger and the pull portion is detached from the proximal end through hole of the clip piece whereby a separation of the release member from the clip piece is completed.

5. The release device for medical tissue clips according to claim 1, wherein the push portion of the one release member is made of an elastic material, such that when a pulling force is applied to the release member, the push portion is compressively deformed and then becomes smaller, and the push portion slides through the proximal end through hole of the clip piece, to make the proximal end through hole of the clip piece located between the push portion and the pull portion of the release member such that the release member can push the clip piece and the clip base out of the outer tube.

6. The release device for medical tissue clips according to claim 1, wherein the pull portion of the one release member is made of an elastic material, such that when a pulling force applied to the release member is greater than a preset value, the pull portion is compressively deformed and then becomes smaller, and the pull portion is detached from the proximal end through hole of the clip piece, whereby a separation of the release member from the clip piece is completed.

7. The release device for medical tissue clips according to claim 1, wherein the pull portion of the one release member is a first protrusion portion, the push portion is a second protrusion portion, a groove portion is provided at a proximal end of the first protrusion portion, a diameter of the groove portion is smaller than diameters of the first protrusion portion and the second protrusion portion, a diameter of a joint between the groove portion and the first protrusion portion gradually increases from a proximal end of the joint to a distal end of the joint, a diameter of a proximal end portion of the second protrusion portion gradually decreases from the distal end to the proximal end, and a first abutment surface is provided at a joint between the groove portion and the second protrusion portion.

8. The release device for medical tissue clips according to claim 7, wherein the elastic member of the clip base is a first blade, the clip base is further provided with a clip base slot, the clip piece comprises two clip piece bodies, wherein the two clip piece bodies are provided with a proximal end through hole which is the first hole matched with the one release member, and a distal end through hole which is the second hole, second blades matched with the clip base slot is provided at two sides of the first hole, and a clip piece end surface matched with a first abutment surface of the release member is provided at the proximal end of the clip piece.

9. The release device for medical tissue clips according to claim 8, wherein each of distal ends of the two clip piece bodies is provided with a semi-circular through hole when the clip piece is in the opened state, and when the clip piece is in the locked state where the two clip piece bodies are closed, the two semi-circular through holes at the distal ends of the two clip piece bodies form the second hole.

10. The release device for medical tissue clips according to claim 9, wherein a diameter of the first protrusion portion of the release member is larger than a diameter of the second protrusion portion, and the diameter of the second protrusion portion is larger than an inner diameter of the first hole of the clip piece.

11. The release device for medical tissue clips according to claim 10, wherein when the clip piece is in the locked state where the two clip piece bodies are closed, an inner diameter of the second hole formed at the distal end is larger than the diameter of the first protrusion portion of the one release member.

12. The release device for medical tissue clips according to claim 1, wherein the distal end of the outer tube is provided with a support cap, and the support cap is provided with a second abutment surface.

13. The release device for medical tissue clips according to claim 1, wherein the one release member is connected to a handle via the control wire, a handwheel is disposed outside the handle, and a gear, a rack, a drive tube and a boosting tube are disposed in the handle; and the handwheel is configured to rotate to sequentially drive the gear, the rack, the drive tube, the boosting tube and the control wire, and the control wire is configured to drive the one release member.

* * * * *